Figure 1:
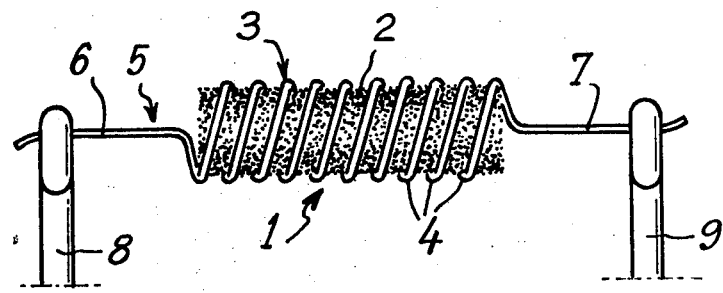

United States Patent [19]

Lacroix et al.

[11] 4,077,775
[45] Mar. 7, 1978

[54] ELEMENT FOR DETECTING THE PRESENCE OF COMBUSTIBLE GASES IN A GASEOUS ATMOSPHERE

[75] Inventors: Roger Lacroix, Suresnes; Manfred Wacker, Montsoult; Claude Lambert, Paris, all of France

[73] Assignee: Comptoir Lyon-Alemand-Louyot, France

[21] Appl. No.: 737,707

[22] Filed: Nov. 1, 1976

[30] Foreign Application Priority Data

Dec. 5, 1975 France .............................. 75 37332

[51] Int. Cl.² .......................................... G01N 27/16
[52] U.S. Cl. .................................... 23/254 E; 338/34
[58] Field of Search .................... 23/254 E, 232 E; 338/34; 340/237 R; 73/23, 27 R

[56] References Cited

U.S. PATENT DOCUMENTS

| 2,768,069 | 10/1956 | Thompson | 23/232 E UX |
|---|---|---|---|
| 3,092,799 | 6/1963 | Baker | 23/254 E X |
| 3,440,017 | 4/1969 | Palmer | 23/232 E X |

FOREIGN PATENT DOCUMENTS 1,506,941   11/1967   France.

OTHER PUBLICATIONS

Hackh's Chemical Dictionary, 4th ed., McGraw-Hill, p. 528.

*Primary Examiner*—Robert M. Reese
*Attorney, Agent, or Firm*—Weingarten, Maxham & Schurgin

[57] ABSTRACT

Element for detecting the presence of combustible gases in a gaseous atmosphere containing at least one oxidizing agent, comprising a microporous support consisting essentially of a mixture of gamma-and/or eta-alumina and refractory fibres, a catalyst layer based on a metal or an oxide of a metal from the family of the platinoids, located on at least a part of the surface of the microporous support, and a filament based on platinum, of which at least a part is wound round the said support.

8 Claims, 6 Drawing Figures

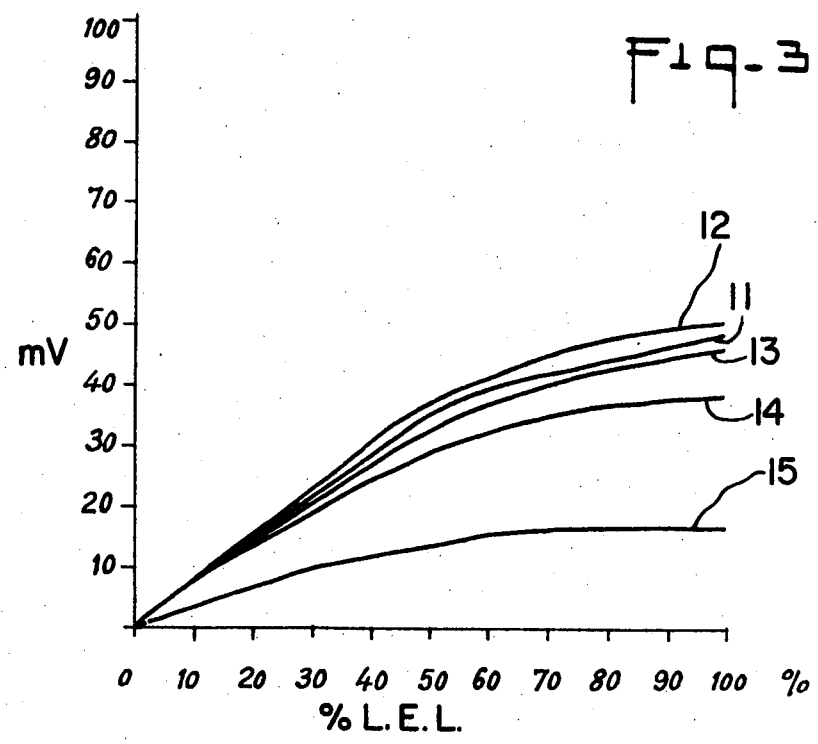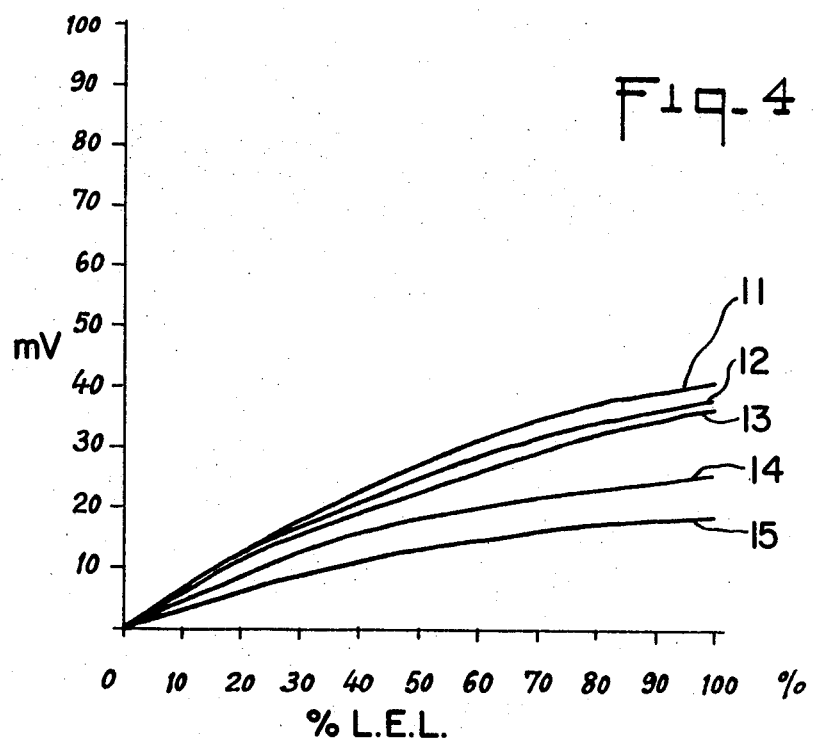

ELEMENT FOR DETECTING THE PRESENCE OF COMBUSTIBLE GASES IN A GASEOUS ATMOSPHERE

The present invention relates to an element for detecting the presence of combustible gases in a gaseous atmosphere containing at least one oxidising agent.

In effect, the subject of the invention is the sensitive element of devices intended to signal the presence of combustible gases in the air before this presence has dangerous consequences such as explosions, fires or poisoning effects.

It is known that certain gases which are evolved naturally in mines, or which are accidentally emitted through leaks in industrial or domestic installations, form explosive mixtures with air if their concentration reaches and exceeds a lower limit called the "lower explosive limit" (L.E.L). These gases are most commonly methane $CH_4$, the principal constituent of natural gas and of firedamp, of which the L.E.L. is 5% by volume, propane $C_3H_8$, of which the L.E.L. is 3% by volume, and butane $C_4H_{10}$, of which the L.E.L. is 2% by volume.

Hydrogen has a markedly higher L.E.L. but it can cause fires before its concentration has reached this value. One therefore takes into consideration its "lower limit of inflammability" or L.L.I., which is 4.1% by volume. Other combustible gases such as carbon monoxide present a hazard through their toxicity. The limiting contents which can be tolerated without trouble are therefore very low, namely 0.005% by volume in the case of carbon monoxide. To ensure against the dangers of explosion or fire, it is generally considered that leaks or evolutions of combustible gases must be detected as soon as the concentrations of these gases in the atmosphere reaches 10% of their L.E.L. or L.L.I., and these concentrations are thus 0.5% by volume for $CH_4$, 0.3% by volume for $C_3H_8$, 0.2% by volume for $C_4H_{10}$ and 0.41% by volume for $H_2$.

It is known, in the prior art, to use a detecting element which is kept in contact with an oxidation catalyst of which the electrical resistance varies with the temperature.

The electrical assembly which includes such a detecting element in general comprises two platinum resistances which have the same value (of resistance) when they are at the same temperature. These resistances are, for example, placed in two arms of a balanced Wheatstone bridge. One is catalytically inactive whilst, on the other hand, the other is in contact with an oxidation catalyst. This latter resistance rises in temperature when a combustion takes place as the result of the presence of a combustible gas in the atmosphere. It is this rise in temperature which causes the unbalancing of the bridge.

The catalytic effect cannot come into play at ambient temperature, even with the best catalysts known. It does not manifest itself unless the catalyst is at a certain temperature, for example 500° C. It is thus necessary that an electrical current, which raises the inactive resistance and the catalytic resistance to the desired temperature in the absence of combustible gases in the atmosphere, should permanently pass through the bridge.

The invention relates to a new detecting element of the type described above which exhibits reliability, stability of the sensitive resistance and of the catalyst in respect of not varying with time, resistance to atmospheric pollution, especially towards sulphur, and excellent sensitivity.

The invention in effect relates to an element for detecting the presence of combustible gases in a gaseous atmosphere containing at least one oxidising agent, characterised in that it comprises:

a microporous support consisting essentially of a mixture of gamma- and/or eta-alumina and refractory fibres, a catalyst layer based on a metal or an oxide of a metal from the family of the platinoids, located on at least a part of the surface of the microporous support, and a filament based on platinum, of which at least a part is wound round the said support.

The microporous support of the catalyst is thus located inside the coil formed by the turns of the filament based on platinum, and preferably the support at no point extends beyond the coil, either laterally or at the ends.

The microporous support can be positioned inside the coil formed by the filament in the form of an aqueous paste based on alumina monohydrate, preferably in the form of boehmite, and of refractory fibres, for example of asbestos, alumina or kaolin. The paste is subsequently dried and baked at about 700° C and the alumina monohydrate is converted to gamma-or eta-alumina.

The actual catalyst, present on the surface of the microporous support, consists of a fine layer of a metal or of an oxide of a metal of the family of the platinoids.

A preferred catalytic combination, because of its stability and its particular efficiency, especially for the oxidation of gas which is very difficult to oxidise, namely methane, is a mixture of platinum and palladium.

The catalyst combination can respectively contain between 5 and 90%, preferably 15 and 50%, by weight of platinum relative to the total weight of platinum plus palladium.

The catalyst layer can be deposited by any suitable means. However, it is possible to use the particularly advantageous process described in French Patent No. 71/13,010 and in its first certificat of addition 71/47,738.

In using the process described in these patents, a thin continuous film of a particular organic solution of certain organic compounds of the platinoids is deposited on the surface of the microporous support before or preferably after it is baked, deposition being effected, for example, by dipping followed by draining. After calcining the support, the organic matter is destroyed and the desired uniform catalyst layer, exhibiting very high dispersion, is obtained. Another advantage of the use of this process is the possibility of producing perfectly homogeneous simultaneous deposits of several metals (for example a platinum-palladium combination). The detecting element is generally of small size. The coil is preferably produced in the shape of a regular spiral. Thus, the filament based on platinum can be a wire having a diameter of 0.01 to 0.5 mm and preferably of 0.02 to 0.2 mm. The turns of the spiral, the number of which is preferably between 5 and 20, have a diameter of between 0.1 and 5 mm, preferably between 0.2 and 1 mm. The pitch of the spiral can advantageously be between 0.05 and 0.3 mm. The total length of the spiral is preferably between 1 and 5 mm. It is preferable to avoid the use of a platinum alloy, which would have the effect of reducing the temperature coefficient of the resistivity. Pure platinum can be used. Advantageously, a wire of platinum reinforced by dispersion of a material which is completely insoluble in this metal, such as, for example, a refractory oxide for the purpose of improving the rigidity and the mechanical stability, can be used.

The detecting element according to the invention exhibits very good stability, in respect of not varying with time, because of the presence of the solid and non-contaminating microporous support which serves as a support for the actual catalyst layer and as mechanical support to the resistant filament based on platinum, preventing it from bending and flowing, under its own weight, when hot.

The detecting element according to the invention exhibits very good sensitivity because of the close contact which exists between the supported catalyst layer and the filament, and because the catalyst material is preferably located inside the spiral formed by the filament.

The detecting element according to the invention can be used with very great safety because of the small size of the filament which, in combination with the not very high value of the temperature of this filament required for the functioning of the catalyst, makes it possible to feed the electrical circuit with currents of very low intensity under a voltage which is also very low. In order that the detector should not act as a detonator and in order to shield it from air streams, the detector is preferably enclosed in a porous cover.

The microporous support preferably comprises about 15 to 75% by weight of refractory fibres, relative to the gamma- or eta-alumina. Furthermore, the said fibres advantageously have a length of 25 to 100 microns and a diameter of 2 to 5 microns, on average 3 microns.

It is preferred to use a detecting element according to the invention which is of very small size so as to minimise the heat conduction and heat inertia and consequently increase the speed of response.

Furthermore, a detector of small size only requires low electrical power, which increases its safety in use.

The weight of catalyst substance deposited on an element according to the invention is, for example, in the case of platinum or of a mixture of platinum and palladium, about 20 to 100 $\mu$g of the said substance, preferably 20 to 40 $\mu$g, per mm$^2$ of surface area of the support.

Other advantages and characteristics of the invention will emerge on reading the examples which follow, which are given by way of illustration and without implying any limitation, reference being made to the attached drawing in which:

FIG. 1 is an enlarged view of an element according to the invention.

Figure 2:
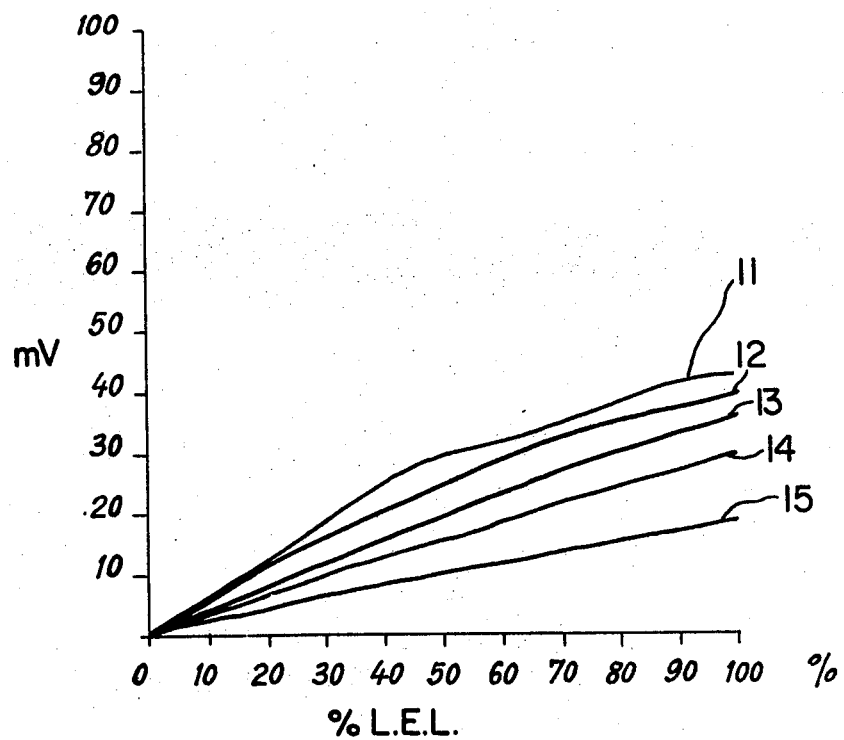

FIGS. 2, 3 and 4 give values of the unbalance voltage which appears at the terminals of an initially balanced bridge circuit of a detecting element according to the invention, for methane, propane and butane respectively.

Figure 5:
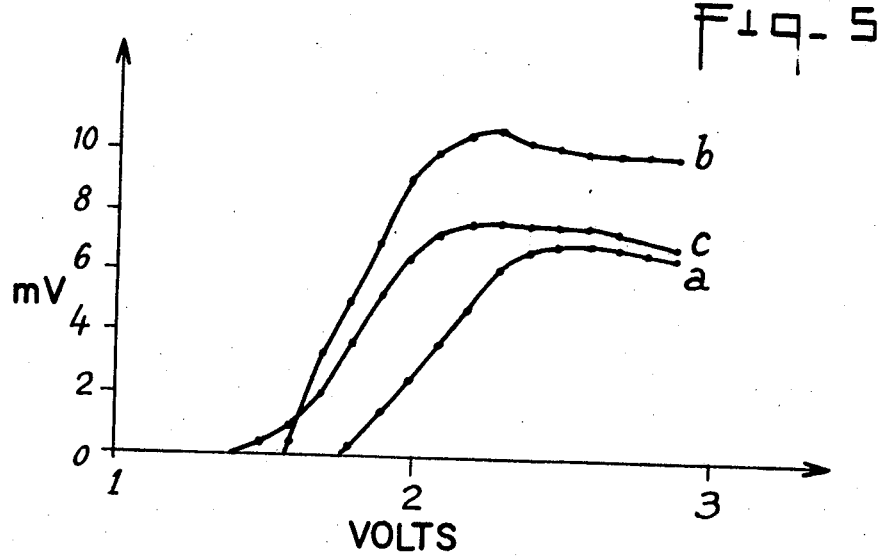
Figure 6:
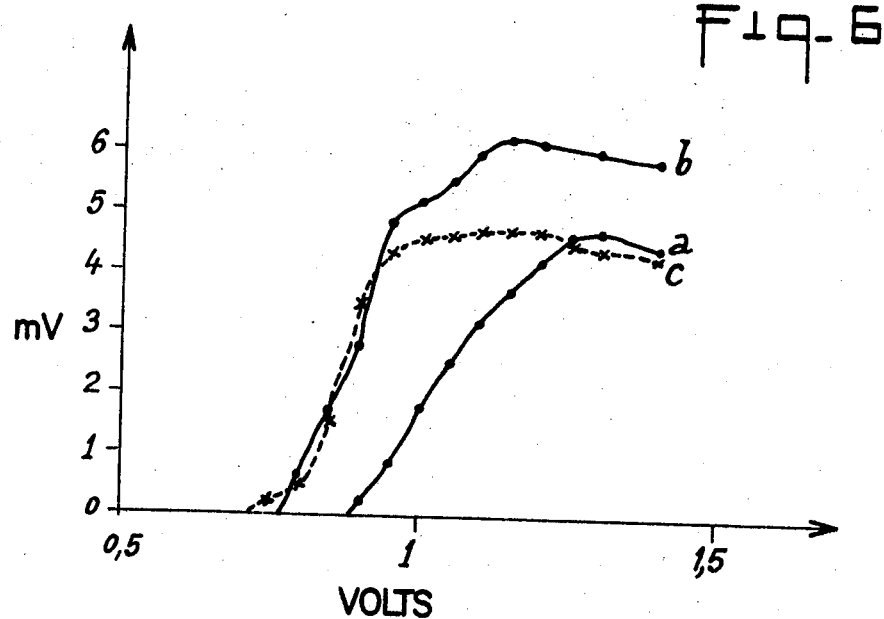

FIGS. 5 and 6 show, for the three gases above, present in the atmosphere at a concentration of 10% of the L.E.L., the values of the unbalance voltages of the bridge, the platinum filament of the detecting element according to the invention being respectively made of "Plativer OY" and of pure platinum.

FIG. 1 shows that a gas-detecting element 1, according to the invention, comprises a microporous support 2 coated on its surface with a catalyst layer and located inside the spiral 3 formed by the turns 4 of the platinum-based filament 5.

The spiral 3 is extended, at each of its ends, by two segments of filaments, 6 and 7, which are left straight.

The element 1 is located on two devices 8 and 9, which are supports which also provide for the passage of the electric current.

EXAMPLE 1

A spiral consisting of ten turns of pure platinum wire (temperature coefficient of the resistivity between 0° and 100° C: greater than or equal to $3.920 \times 10^{-3}$) is produced. Diameter of this wire: 0.1 mm. External diameter of the spiral : 0.6 mm. Pitch of the spiral : 0.18 mm. The spiral is 1.8 mm long; it is extended, at each end, by a length of 3 mm of platinum wire which is left straight. Its resistance is 0.3 $\Omega$ at ambient temperature. The microporous support of the catalyst is produced by calcining a paste having the following composition:

| | |
|---|---|
| "GB 200" alumina | 55 g |
| Ground "Fibral 80" - fraction (100 $\mu$m | 28 g |
| Water | 17 g |
| | 100 g |

"GB 200" alumina is a mixture of boehmite and aluminum nitrate manufactured by Rhone Poulenc. It is in the form of a thixotropic paste containing 17% of Al$_2$O$_3$. "Fibral 80" is a cake of very friable ceramic fibres supplied by Societe Generale des Produits Refractaires (S.G.P.R.). The paste obtained by grinding the above mixture is introduced inside the spiral, avoiding any external overflow. After drying, the material is calcined by gradually raising it to 700° C in air. During this calcination, the boehmite is dehydrated to gamma- or eta-alumina. Because of the ceramic fibres provided by the "Fibral 80", no shrinkage cracks appear during the baking.

The element thus obtained is dipped in a solution of platinum sulphoresinate and palladium sulphoresinate so as to produce a catalyst deposit of 10 to 50 $\mu$g, containing about 25% by weight of platinum and 75% of palladium, on the microporous support after calcination at about 500° C.

The detecting element thus produced is placed, as a resistance, in one arm of an initially balanced electrical bridge circuit.

The voltage applied to the bridge is 1.2 V and the intensity of the current which flows through it when it is balanced is 0.85 A. The resistance of the filament, the temperature of which is about 400° C, is 0.75 $\Omega$. The signal emitted when combustible gases are present in the atmosphere consists of an unbalance voltage which appears at the terminals of the bridge. The curves of FIGS. 2, 3 and 4 give the values which the voltage reaches as a function of the % of the L.E.L. and the variation in these values in the course of continuous operation in the case of the three gases, methane, propane and butane. Each of these figures is a plot of the percentage of lower explosive limit (L.E.L.) as the abcissa against voltage in millivolts (mV) as the ordinate. In each of the figures, the response curves are identified as follows: the curve referred to by reference numeral 11 is the initial curve or the value at time T = 0; curve 12 represents operation of the detector in the atmosphere for 1 month; curve 13 represents operation of the detector for 2 months; curve 14 represents operation of the detector for 4.5 months; and curve 15 represents operation of the detector for 10 months. FIG. 3 evidences a spontaneous reversal between the one month curve and the initial curve. It is to be understood that these figures relate to a particular example and these values can vary by ± 10% from one manufacturing batch to another.

EXAMPLE 2

The pure platinum of Example 1 is replaced by a platinum reinforced by dispersion of a refractory oxide. The gain in solidity thus acquired makes it possible to use a filament of smaller diameter which, in turn, enables the number of turns of the spiral and the electrical resistance of said spiral to be increased, the dimensions of the detector remaining equal.

The increase in resistance of the helix has a number of favourable consequences:

a. this electrical resistance of the spiral becomes greater with respect to that of the junction cable to the bridge feed and signal utilisation devices. The stability and reliability of the device are increased. The cable may be of considerable length.

b. the resistance being greater, its variations, for a given temperature variation and for the same consumption of energy, are considerable. The sensitivity is increased as much.

c. the power supplied to the detector head is obtained under a higher voltage with a lower current, this reducing the line losses and enabling the necessary energy to be maintained at a fairly low level for the dangers of explosion or fire to be even lower in the case of damage accidentally occuring during installation.

The increase in the number of turns of the spiral increases the fraction of the heat produced by the catalytic combustion which is transmitted to this turn, hence a gain in sensitivity.

In this example, "Plativer OY" reinforced platinum from Comptoir Lyon-Alemand, Louyot, in Paris, consisting of pure platinum and 0.15% by weight of $Y_2O_3$ was used to form the sensitive filament.

The filament has a diameter of 0.060 mm. It is wound as a spiral on a mandrel of 0.4 mm diameter. The pitch of this spiral is 0.11 mm and the spiral has 16 turns.

The microporous support and the catalyst layer are the same as those of Example 1.

The feed voltage is 2.6 V and the (current) intensity is 0.39 A.

The initial signal, for concentrations of 10% of the L.E.L., for example has the following values:

methane: 7.2 mV
propane: 10.4 mV
butane: 7.8 mV.

FIG. 5 shows the values of the unbalance voltages (in millivolts) as a function of the feed voltage (in volts) of the bridge for these three gases present in the atmosphere at a concentration equal to 10% of their L.E.L. when the filament is Plativer OY. By way of comparison, FIG. 6 gives the same characteristics when the filament is made of pure platinum, all other conditions remaining the same.

In FIGS. 5 and 6, the curves a, b and c respectively correspond to methane, propane and butane.

EXAMPLE 3

In this example, the influence of certain important parameters on the sensitivity of a detector according to the invention is studied. In this example, the detector and the bridge measuring circuit described in Example 1 above are used.

a. Effect of ambient temperature on the sensitivity of the detector:

This sensitivity is measured by the unbalance voltage of the measuring bridge when the concentration of combustible gas in the atmosphere is equal to 10% of the L.E.L. of this gas. The bridge is fed at a voltage of 1.2 V, to which corresponds a (current) intensity of 0.85 A in the resistance of the detecting element, and the measurements are carried out at ambient temperatures of $-10°$, $+20°$ and $+50°$ C. The combustible gases used are methane, butane and propane. The unbalance voltages, that is to say the response signals, do not vary during these experiments and retain the values of 4mV for $CH_4$, 7mV for $C_3H_8$ and 5mV for $C_4H_{10}$. This insensitivity to ambient temperature is, however obtained only if the feed voltage is chosen so that the operational conditions are such that the unbalance voltage is that of the level parts of the curves of FIGS. 5 and 6.

b. Influence of the feed voltage on the maximum sensitivity of the detector.

As can be seen in FIG. 5, the response signal exhibits a maximum as the feed voltage of the measuring bridge is varied.

It is thus seen that whilst the sensitivity does not seem to vary with ambient temperature for a suitable feed voltage of the bridge, on the other hand, the position of the maximum in the curve will depend on this voltage.

Thus, it has been found by means of the experiments carried out with propane that the sensitivity of the detector is 8mV under 1.4V at 27° C and 10 mV under 1.2 V at $-10°$ C.

c. Effect of an accidental overload

If the detector is accidentally subjected to an atmosphere having a high content of combustible gas, the very high temperature which it reaches alters its sensitivity. This is shown by experiments during which the detector is placed in atmospheres containing methane, propane or butane at concentrations successively raised to 15, 30, 60, 90 and 100% of the volume of gas. After return to an atmosphere where the concentration is 10% of the L.E.L., the response signals have the following values (ambient temperature 20° C) :

for $CH_4$ 2.5 mV in place of 4.5 before overload
for $C_3H_8$ 5 mV in place of 7 before overload
for $C_4H_{10}$ 3.5 mV in place of 6 before overload.

What is claimed is:

1. Element for detecting the presence of combustible gases in a gaseous atmosphere containing at least one oxidising agent, characterised in that it comprises:
    a microporous support consisting essentially of a mixture of gamma- and/or eta-alumina and refractory fibres,
    a catalyst layer based on a metal or an oxide of a metal from the family of the platinoids, located on at least a part of the surface of the microporous support, and
    a filament based on platinum, of which at least a part is a coil wound round said support.

2. Element according to claim 1, characterised in that the whole of said microporous support is located inside said coil.

3. Element according to claim 1, characterised in that said coil forms a spiral.

4. Element according to claim 1, characterised in that said catalyst layer respectively contains between 5 and 90% by weight of platinum and 95 and 10% of palladium.

5. Element according to claim 1, characterised in that said filament is selected from the group consisting of pure platinum and platinum reinforced by dispersion of a refractory oxide.

6. Element according to claim 1, characterised in that said microporous support is produced by calcining an aqueous paste, based on beohmite and refractory fibres, at about 700° C.

7. Element according to claim 1, characterised in that said catalyst layer is obtained by calcining a continuous thin film of a solution of certain organic compounds of the platinoids.

8. Element according to claim 1, characterised in that said filament has a diameter of 0.01 to 0.5 mm, and is wound in the form of a spiral having about 5 to 20 turns of a diameter of between 0.1 and 5 mm, the pitch of the said spiral being between 0.1 and 5 mm and the total length of the said spiral being between 1 and 5 mm.

* * * * *